United States Patent [19]

Kuwada et al.

[11] 4,082,764
[45] Apr. 4, 1978

[54] METHODS FOR THE PRODUCTION OF 4H-s-TRIAZOLO[4,3-a][1,4]BENZODIAZEPINE 5N-OXIDES

[75] Inventors: Yutaka Kuwada, Ashiya; Kanji Meguro, Takarazuka; Hiroyuki Tawada, Kyoto, all of Japan

[73] Assignee: Takeda Chemical Industries, Ltd., Osaka, Japan

[21] Appl. No.: 612,745

[22] Filed: Sep. 12, 1975

Related U.S. Application Data

[60] Division of Ser. No. 482,798, Jun. 24, 1974, Pat. No. 3,927,015, which is a continuation of Ser. No. 255,993, May 23, 1972, abandoned.

[30] Foreign Application Priority Data

Jun. 5, 1971  Japan .................................... 50/39700

[51] Int. Cl.$^2$ ............................................ C07D 487/04
[52] U.S. Cl. .................................................. 260/308 R
[58] Field of Search ..................................... 260/308 R

[56] References Cited

U.S. PATENT DOCUMENTS

| 3,583,978 | 6/1971 | Archer et al. ................. 260/239 BD |
| 3,709,898 | 1/1973 | Hester ............................... 260/308 R |

OTHER PUBLICATIONS

Derieg et al., J. Org. Chem., vol. 36, pp. 782–787 (1971).

*Primary Examiner*—Alton D. Rollins
*Attorney, Agent, or Firm*—Wenderoth, Lind & Ponack

[57] ABSTRACT

The title compounds are prepared by reacting a 3-amino-3,4-dihydro-4-hydroxy-4-phenylquinazoline with a reactive derivative of a halogenoacetic acid, reacting the resultant halogenoacetyl derivative with a weak acid, reacting the resultant 2-(3-halomethyl-s-triazol-4-yl)benzophenone with hydroxylamine and subjecting the resultant 2-(3-hydroxyamino-methyl-s-triazol-4-yl)benzophenone to dehydration to effect ring closure.

3 Claims, No Drawings

METHODS FOR THE PRODUCTION OF 4H-s-TRIAZOLO[4,3-a][1,4]BENZODIAZEPINE 5N-OXIDES

This application is a division of Ser. No. 482,798, filed June 24, 1974, now U.S. Pat. No. 3,927,015 which is a continuation of Ser. No. 255,993, filed May 23, 1972, now abandoned.

The present invention relates to a method for the production of heterocyclic compounds, more particularly relates to a novel and industrially feasible method for the production of heterocyclic compounds of the following general formula (I) or pharmaceutically acceptable acid addition salts thereof, which are useful as medicines, such as tranquilizers, sedatives or hyponotics;

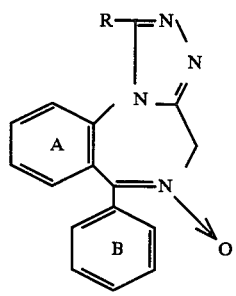

wherein R represents a hydrogen atom or a lower alkyl group, and the rings A and/or B are unsubstituted or substituted by at least one of the members consisting of halogen atom, nitro, trifluoromethyl, lower alkyl or lower alkoxy groups, which can be the same or different.

The method for the present invention, by which the above desired compounds (I) can be produced, comprises reacting a compound of the general formula (III)

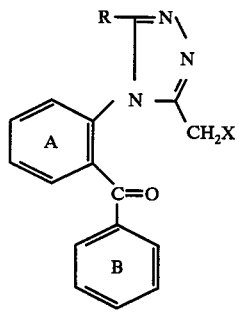

wherein X represents a halogen atom, R and the rings A and B have the same meaning as above, with hydroxylamine to give a compound of the general formula (II)

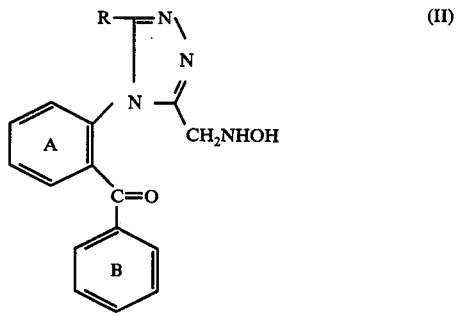

wherein R and the rings A and B have the same meaning as above, and then subjecting the compound of the general formula (II) to a ring-closure reaction.

The reactions involved in the present method are shown in the following schema:

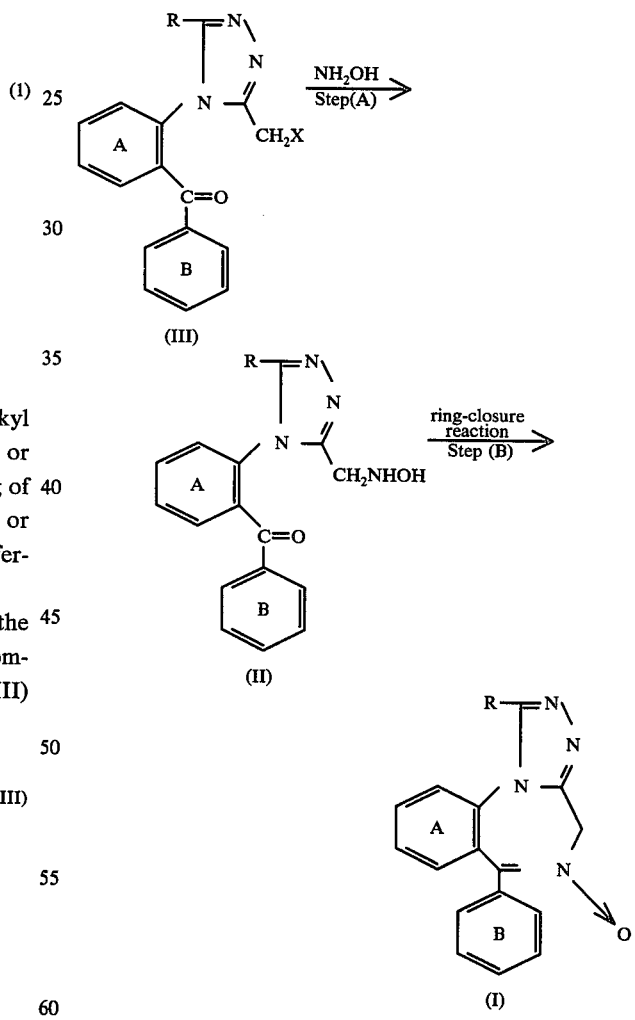

wherein R, X and the rings A and B have the same meaning as above.

Hitherto there have been reported a method for the production of the compounds (I), which is shown by the following schema:

Method (a)

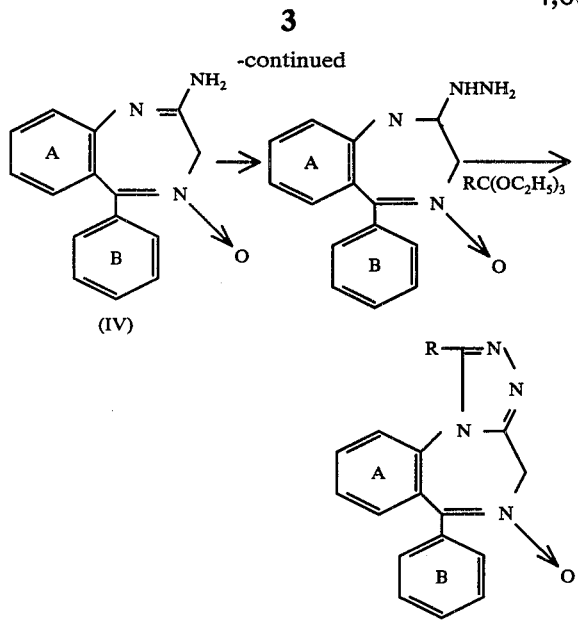

(IV)

wherein R and the rings A and B have the same meaning as above.

And, also for the production of the compound (IV), the following method has been reported:

Method (b)

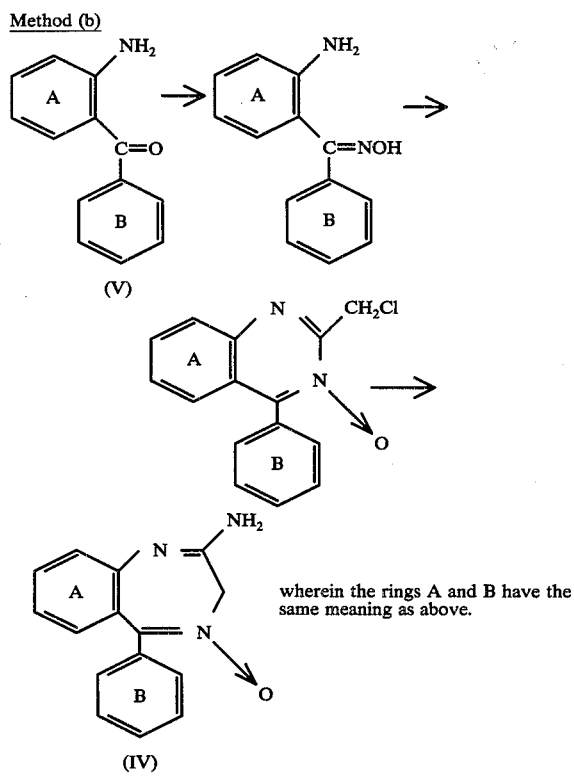

wherein the rings A and B have the same meaning as above.

According to the known method (b), however, the compound (IV) is obtained only at a poor yield, and threrefore, in case of producing the compounds (I) by combination of the above known method (a) with the known method (b), the overall yield of the compounds (I) starting from the compounds (V) is rather low. Thus, the above known methods are not statisfactory from an industrial point of view.

Under these circumstances, the present inventors have made extensive studies for developing a novel and advantageous route for the production of the compounds (I).

As a result of the studies, the present inventors have unexpectedly succeeded in synthesizing the novel compounds (III) from the compounds (V) in a high yield, and also found that the compounds (I) can be produced in only two steps and in a quite satisfactory yield by employing any of these novel compounds (III) as a starting compound. The present invention has been accomplished on the basis of these findings.

Thus, according to the present method, the desired compounds (I) can be easily produced in a high yield by only two simple steps, and therefore, the present method is effectively and advantageously feasible from an industrial point of view.

Namely, the principal and essential object of the present invention is to provide a novel and industrially feasible method for the production of the desired compounds (I), and this object is accomplished by using a novel compound (III), which is first synthesized by the present inventors, as a starting compound for the production of the compound (I).

In the following, explanation of the present method is given.

In the above general formulas, as the lower alkyl group represented by the symbol R, preferable ones are those having up to three carbon atoms, which include methyl, ethyl, propyl and isopropyl group. Among the above groups, methyl group is especially preferable from a practical point of view. The halogen atom represented by the symbol X includes, for example, chlorine, bromine and iodine.

The rings A and/or B are unsubstituted or substituted in their optional position(s) by one or more substituents, which can be the same or different, selected from halogen atom (i.e. fluorine, chlorine, iodine and bromine), nitro, trifluoromethyl, lower alkyl or lower alkoxy group. As the lower alkyl group, preferable ones are those having up to three carbon atoms, which include the same lower alkyls represented by the symbol R. As the lower alkoxy group, preferable ones are those having up to three carbon atoms, which includes methoxy, ethoxy, propoxy and isopropoxy group.

In the present method the reaction of Step (A) is conducted by reacting a 2-(3-halogenomethyltriazolyl)-benzophenone derivative (III) with hydroxylamine in the absence or presence of a suitable solvent.

The amount of hydroxylamine is generally about 1 to about 20 moles per mole of the compound (III). Hydroxylamine may be employed in the reaction in a form of a free base or in a form of its acid addition salt (e.g. hydrochloride, sulfate), though the former is preferable. In case where an acid addition salt of hydroxylamine is used in the reaction, it is preferable to add the salt to the reaction system after neutralizing it with a suitable basic substance or to add the salt to the reaction system together with a suitable basic substance. As the basic substance, there may be, for example, alkali metal hydroxides (e.g. sodium hydroxide, potassium hydroxide), alkalimetal carbonates or bicarbonates (e.g. sodium carbonate, potassium carbonate, sodium bicarbonate and potassium bicarbonate) and tertiary amines (e.g. triethylamine, pyridine). In the present reaction, it is also preferable to add to the reaction system an excess amount of the basic substance as an acid acceptor in order to remove a hydrogen halide generated during the reaction. The solvent which may be used in this reaction includes, for example, alcohols (e.g. methanol, ethanol, propanol), hydrocarbons or halogenated hydrocarbons (e.g. chloroform, dichloromethane, benzene, toluene), tertiary amines (e.g. pyridine) and dimethylformamide. The reaction conditions such as temperature and time are not limited, but the reaction of the present step is preferably conducted at about 60° to 80° C, and, if necessary, it may be conducted at a temperature higher or lower than the above-mentioned range. The reaction time is usually about 0.5 to 10 hours.

Further, in case where a starting compound (III) wherein X is chlorine or bromine is used in the present step, in order to accelerate the reaction, it is sometimes preferable that the starting compound (III) is converted to that wherein X is iodine by reacting the starting compound (III) with a slight excess amount of alkali metal iodide (e.g. sodium iodide, potassium iodide), and then the thus converted compound (III) is used in the reaction, or it is sometimes preferable to conduct the present reaction in the presence of the above-mentioned alkali metal iodide. In the latter case, the amount of the alkali metal iodide is usually about 0.1 to about 1 mole per mole of the compound (III).

The thus produced intermediate compound (II) is employable as the starting compound of Step (B) without isolating it from the reaction mixture of Step (A). But, if necessary, the thus produced compound (II) is easily isolated in an optional purity, namely, sometimes as crystals, by per se conventional means such as extraction with a suitable solvent (e.g. ethyl acetate, chloroform, dichloromethane), recrystallization and chromatography.

In Step (B), the compound (II) is subjected to a ring-closure reaction. The present ring-closure reaction is preferably conducted in the presence of a solvent, and as the solvent there may be mentioned the same ones as employed in the reaction of Step (A). The reaction conditions such as temperature and time are not limited, but it is practically preferable to conduct the present reaction at about 10 to about 80° C or up to around the boiling point of the solvent used (i.e. under reflux). The temperature, if necessary, may be lower or higher than that mentioned above. The reaction time is usually about 5 minutes to 10 hours. While the present reaction can usually proceed at any of basic, neutral or acid range, it is practically preferable to add an acid substance to the reaction system in order to accelerate the reaction. As the acid substance, there may be counted, an inorganic acid (e.g. hydrochloric acid, hydrobromic acid, sulfuric acid) and an organic acid such as lower carboxylic acid (e.g. acetic acid, propionic acid) and organic sulfonic acid (e.g. p-toluensulfonic acid, methansulfonic acid).

By the process as mentioned above, the ring-closure reaction proceeds under dehydration to give the desired compound (I).

As mentioned above, in order to obtain the desired compounds (I) in a high yield, it is practically preferable to conduct successively the reactions of Step (A) and Step (B) without isolation of the intermediate compound (II) which is produced in the former step. For example, the desired compound (I) can be produced by reacting at first a compound (III) with hydroxylamine to give an intermediate compound (II) in the reaction mixture of Step (A), and then by heating the reaction mixture thus obtained without isolation of the produced compound (II). Further, it is also practically preferable to add the above acid substance to the reaction system at a suitable stage of the above procedure in order to accelerate the ring-closure reaction of Step (B). The stage at which the acid substance is added to the reaction system is selected adequately from any time after the starting compound (III) has been reacted with hydroxylamine to give the intermediate compound (II), or a mixture of the compound (II) and the desired compound (I). The reaction from the compounds (III) to (I) through (II) during the above procedure can be easily traced by the means of a thin layer chromatography.

In case where the thus produced compounds (I) are obtained in a form of free base, if necessary, they can be converted to the corresponding acid addition salts by treating them with a suitable acid after per se conventional means. As the acid, there may be, for example, an organic acid (e.g. tartaric acid, succinic acid), and an inorganic acid (e.g. hydrochloric acid, hydrobromic acid, sulfuric acid).

The thus produced compounds (I) or pharmaceutically acceptable acid addition salts thereof show an effect upon the central nervous system such as muscle relaxing, anticonvulsive, analgetic, sedative and hypnotic actions, and therefore they are useful as medicines such as muscle relaxant, anticonvulsant, analgetic agent, sedatives and hypnotics.

The compounds (I) or pharmaceutically acceptable acid addition salts thereof are administered per se orally or parenterally or, if necessary, mixed with pharmaceutically acceptable carrier or adjuvent in a suitable pharmaceutical form such as powder, granule, tablet, suppository, syrup and injection. The dosage may vary with the types of the compounds (I) and the symptoms of diseases, but the usual daily dosage for an adult human is generally from about 1 to 30 mg.

The compounds (I) are also useful as the intermediates for the production of other medicines, for example 4-hydroxy- or 4-alkoxy-triazolebenzodiazepine derivatives, having activities on the central nervous system.

The starting compounds (III) of the present method can be, for example, produced by the reaction steps described below:

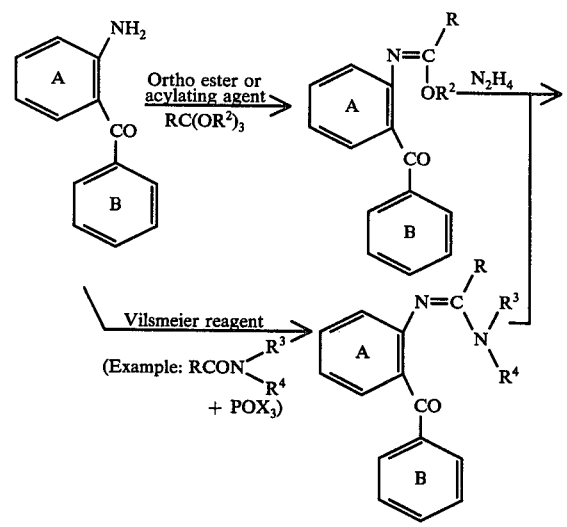

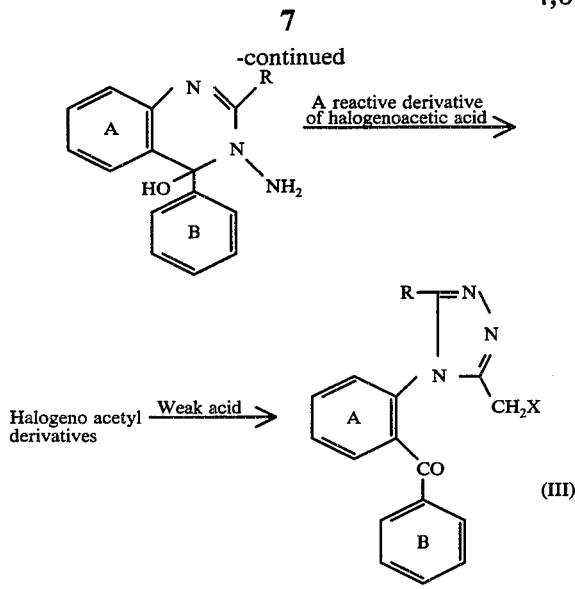

(wherein R² is a hydrogen atom or a lower alkyl group, R³ and R⁴ are the same or different lower alkyl group, X and R and rings A and B have the same meaning as mentioned above).

In these reactions, the acylating agent is exemplified by formic acid, acetic acid, and acid halides and acid anhydrides derived from an acid of the formula RCOOH where R is a hydrogen atom or a lower alkyl group, preferably having 1 to 3 carbon atoms such as methyl, ethyl, n-propyl and isopropyl; the reactive derivative of halogenoacetic acid is an acid halide or acid anhydride derived from a haloacetic acid of the general formula ZCH₂COOH where Z is a halogen atom such as chlorine, bromine and iodine; and the weak acid is exemplified by aliphatic carboxylic acids (e.g. formic acid, acetic acid, monochloroacetic acid, dichloroacetic acid, propionic acid and butyric acid), aromatic carboxylic acids (e.g. benzoic acid and salicylic acid) and aromato-aliphatic carboxylic acids (e.g. phenylacetic acid).

For further explanation of the present invention, the following Examples are given, wherein the term "part(s)" is based on weight unless otherwise noted and the relationship between "part(s)" and "volume part(s)" corresponds to that between "gram(s)" and "milliliter(s)".

EXAMPLE 1

(a) A solution of 34.7 parts of 2-amino-5-chlorobenzophenone in 100 volume parts of formic acid is refluxed for 1.5 hour, and the excess formic acid is distilled off under reduced pressure. The residue is dissolved in 30 volume parts of ethyl acetate, and washed with a saturated aqueous solution of sodium bicarbonate and water in this order, and dried over sodium sulfate, followed by distilling off the solvent. Treatment of the residue with n-hexane gives 5-chloro-2-formamidobenzophenone as pale yellow crystals. Recrystallization of the crystals from ethanol gives pale yellow granules melting at 92.5° to 93° C. Yield: 98%

Elemental analysis $C_{14}H_{10}ClNO_2$: Calculated: C, 64.74; H, 3.88; N, 5.39. Found: C, 64.84; H, 3.55; N, 5.16.

(b) To a solution of 2.7 parts of 5-chloro-2-formamidobenzophenone in 40 volume parts of ethanol is added 2.5 volume parts of hydrazine hydrate, followed by refluxing for 20 minutes. After cooling, the resulting crystals are recovered by filtration and washed with ethanol and ether and then dried. This procedure gives 3-amino-6-chloro-3,4-dihydro-4-hydroxy-4-phenylquinazoline as crystals melting at 189° to 192° C. Yield: 95%.

Elemental analysis: $C_{14}H_{12}ClN_3O$: Calculated: C, 61.43; H, 4.42; N, 15.35. Found: C, 61.34; H, 4.22; N, 15.22.

(c) A mixture of 68.4 parts of thus obtained crystals, 75 parts of anhydrous sodium carbonate, 600 volume parts of water and 600 volume parts of chloroform is cooled with ice-salt, and to the mixture is added dropwise 60 volume parts of chloroacetyl chloride under stirring within 30 minutes below 10° C. After stirring for further 20 minutes, the resulting precipitates are recovered by filtration and washed with water and chloroform and then dried. This procedure gives bis(-monochloroacetyl) derivative of 3-amino-6-chloro-3,4-dihydro-4-hydroxy-4-phenylquinazoline as crystals. Recrystallization from chloroform-methanol gives colorless needles melting at 157° to 158° C. Yield: 93%.

Elemental analysis: $C_{18}H_{14}Cl_3N_3O_3$: Calculated: C, 50.66; H, 3.14; N, 9.85. Found: C, 50.34; H, 3.31; N, 9.80.

The same product as above is obtained also by conducting the chloroacetylation with monochloroacetic anhydride in pyridine.

(d) To 250 volume parts of acetic acid is added 12.8 parts of the bis-(monochloroacetyl) derivative of 3-amino-6-chloro-3,4-dihydro-4-hydroxy-4-phenylquinazoline, and the mixture is refluxed for one hour. The excess acetic acid is distilled off under reduced pressure, and the residue is neutralized with a saturated aqueous solution of sodium bicarbonate and extracted with ethyl acetate. The ethyl acetate layer is washed with water and dried over sodium sulfate, followed by distilling off the ethyl acetate. The residue is dissolved in a mixture of ethanol and ether, and saturated ethanolic hydrogen chloride is added thereto. The precipitated crystals are recovered by filtration, washed with ether and small amount of acetone in this order and then dried, whereby 5-chloro-2-(3-chloromethyl-s-triazol-4-yl) benzophenone is obtained as crystals of a hydrochloride. Recrystallization from a mixture of ethanol and ether gives colorless crystals melting at 176° to 178° C. Yield: 80%.

Elemental analysis $C_{16}H_{11}Cl_2N_3O\cdot HCl$: Calculated: C, 52.13; H, 3.28; N, 11.40. Found: C, 52.27; H, 2.94; N, 11.17.

EXAMPLE 2

(a) To a mixture of 2.3 parts of 2-amino-5-chlorobenzophenone, 20 volume parts of chloroform and 4 volume parts of dimethylformamide is added dropwise 3.7 volume parts of thionylchloride under stirring, followed by stirring further 30 minutes at room temperature. To the resulting mixture is added ice-water and the whole mixture is neutralized with a saturated aqueous solution of sodium bicarbonate, followed by recovering the chloroform layer. The aqueous layer is further subjected to extraction with chloroform. The two chloroform layers are combined, washed with water and dried over sodium sulfate, and then the solvent is distilled off. The residue is treated with n-hexane, whereby 5-chloro-2-dimethylaminomethylenaminobenzophenone are obtained as crystals. Recrystallization from isopropylether gives pale yellow needles melting at 86° to 87° C. Yield: 95%

Elemental analysis $C_{16}H_{15}ClN_2O$: Calculated: C, 67.01; H, 5.27; N, 9.77. Found: C, 67.15; H, 5.43; N, 10.01.

(b) To a solution of 0.29 part of 5-chloro-2-dimethylaminomethyleneaminobenzophenone in 4 volume parts of ethanol are added 0.2 volume part of hydrazine hydrate and 0.06 volume part of glacial acetic acid. The mixture is shaken and kept standing at room temperature for about 30 minutes. The resulting crystals are recovered by filtration and washed with ethanol and then dried, whereby 3-amino-6-chloro-3,4-dihydro-4-hydroxy-4-phenylquinazoline is obtained as colorless needles melting at 185° (softening) to 192° C. This compound is identical with the product obtained in Example 1. Yield: 95%.

(c) The crystals are reacted with chloroacetylchloride in the same manner as Example 1 to give a bis-(monochloroacetyl) derivative of 3-amino-6-chloro-3,4-dihydro-4-hydroxy-4-phenylquinazoline melting at 157° to 158° C. The bis-(monochloroacetyl) derivative is reacted with acetic acid and treated in the same manner as Example 1, whereby 5-chloro-2-(3-chloromethyl-s-triazol-4-yl) benzophenone is obtained as a hydrochloride melting at 176° to 178° C. Yield: 74.4%.

EXAMPLE 3

(a) A solution of 11.5 parts of 2-amino-5-chlorobenzophenone, 11.5 parts of ethyl orthoacetate and 6 volume parts of acetic acid in 100 volume parts of benzene is refluxed for 20 minutes, whereby 5-chloro-2-(1-ethoxyethylideneamino)-benzophenone are obtained as crystals. Recrystallization from methanol-water gives colorless needles melting at 62° to 63° C. Yield: 93%.

Elemental analysis $C_{17}H_{16}NO_2$: Calculated: C, 67.66; H, 5.34; N, 4.64. Found: C, 67.65; H, 5.42; N, 4.29.

(b) To a solution of 3 parts of the crystals obtained in the above step (a) in 30 volume parts of ethanol are added 15 volume parts of hydrazine hydrate and 0.6 volume part of acetic acid. The mixture is stirred for 6 hours, whereby 3-amino-6-chloro-3,4-dihydro-4-hydroxy-2-methyl-4-phenylquinazoline are obtained as crystals. Recrystallization of the crystals from chloroform-methanol gives colorless prisms melting at 205° to 208° C. Yield: 92%.

Elemental analysis $C_{15}H_{14}ClN_3O$: Calculated: C, 62.61; H, 4.90; N, 14.60. Found: C, 62.77; H, 4.76; N, 14.21.

(c) To 50 volume parts of benzene are added 2.9 parts of the crystals of the quinazoline derivative obtained in the above step (b) and 6.6 parts of 2-methylimidazole, followed by adding dropwise 3.2 volume parts of chloroacetyl chloride under ice-cooling and stirring. This procedure gives crystals of 6-chloro-3-chloroacetylamino-3,4-dihydro-4-hydroxy-2-methyl-4-phenylquinazoline. Recrystallization of the crystals from dimethylformamide-water gives yellow prisms melting at 142° to 145° C. Yield: 81%.

Elemental analysis $C_{17}H_{15}Cl_2N_3O_2$: Calculated: C, 56.06; H, 4.15; N, 11.54. Found: C, 56.00; H, 4.28; N, 11.48.

(d) A solution of 33 parts of 6-chloro-3-chloroacetylamino-3,4-dihydro-4-hydroxy-2-methyl-4-phenylquinazoline in 500 volume parts of formic acid is refluxed for 2.5 hours, followed by subjecting to distillation to remove the excess formic acid. The resulting residue is neutralized with a saturated aqueous solution of sodium bicarbonate, and extracted with ethylacetate. The ethyl acetate layer is washed with water and dried over sodium sulfate, followed by distilling off the solvent. The resulting product is recovered by filtration and washed with ether and then dried, whereby 5-chloro-2-(3-chloromethyl-5-methyl-s-triazol-4-yl) benzophenone are obtained as crystals. Recrystallization from acetoneether gives colorless granules melting at 140° to 142° C. Yield: 86%.

Elemental analysis $C_{17}H_{18}Cl_2N_3O$: Calculated: C, 58.97; H, 3.78; N, 12.14. Found: C, 59.17; H, 3.78; N, 12.23.

EXAMPLE 4

To a solution of 0.35 part of 5-chloro-2-(3-chloromethyl-5-methyl-s-triazol-4-yl) benzophenone in 5 volume parts of acetone is added 0.15 part of sodium iodide, followed by stirring for 2 hours at room temperature. The resulting precipitate is removed by filtration, and the filtrate is concentrated under reduced pressure. The residue is treated with acetone-ether, whereby crystals of 5-chloro-2-(3-iodomethyl-5-methyl-s-triazol-4-yl) benzophenone are obtained. Recrystallization of the crystals from methanol gives pale yellow prisms melting at 178° to 179° C (decomposition). Yield: almost quantitative.

Elemental analysis $C_{17}H_{13}ClIN_3O$: Calculated: C, 46.65; H, 2.99; N, 9.60. Found: C, 46.89; H, 2.80; N, 9.46.

EXAMPLE 5

A procedure mentioned below is conducted in the same manner as Reference 1.

2-Amino-5,2'-dichlorobenzophenone is reacted with formic acid, whereby 5, 2'-dichloro-2-formylaminobenzophenone (pale yellow granules melting at 106° to 107° C) is obtained. The product is then reacted with hydrazine hydrate, whereby 3-amino-6-chloro-4-(2-chlorophenyl)-3,4-dihydro-4-hydroxyquinazoline (colorless granules melting at 198° C (effervescence)) is obtained. The product is reacted with chloroacetyl chloride, whereby a bis-(monochloroacetyl) derivative of 3-amino-6-chloro-4-(2-chlorophenyl)-3,4-dihydro-4-hydroxyquinazoline (colorless powdery crystals melting at 157° to 158° C) is obtained. Further, the product is treated with monochloroacetic acid in dry benzene under refluxing, whereby crystals of 2-(3-chloromethyl-s-triazol-4-yl)-5, 2'-dichlorobenzophenone are obtained. Recrystallization from chloroform-n-hexane gives colorless granules melting at 139° to 140° C. Overall yield: 34%.

Elemental analysis $C_{16}H_{10}Cl_3N_2O$: Calculated: C, 52.41; H, 2.74; N, 11.46. Found C, 52.26; H, 2.38; N, 11.06.

EXAMPLE 6

A procedure mentioned below is conducted in the same manner as example 1.

2-Amino-5-methylbenzophenone is reacted with methyl orthoacetate, whereby 2-(1-methoxyethylideneamino)-5-methylbenzophenone is obtained. The product is reacted with hydrazine hydrate, whereby 3-amino-3,4-dihydro-2, 6-dimethyl-4-hydroxy-4-phenylquinazoline (colorless peates melting at 192° to 196° C) is obtained. The product is reacted with chloroacetylchloride, followed by the same treatment as Example 1, whereby 3-chloroacetylamino-3, 4-dihydro-2, 6-dimethyl-4-hydroxy-4-phenylquinazoline having ½ mole of water of crystallization (colorless powdery crystals melting at 90° to 93° C) is obtained. The product is heated with acetic acid, whereby crystals of 2-(3- chloromethyl-1-methyl-s-triazol-4-yl)-5-methylbenzophenene are obtained. Recrystallization from benzene gives colorless needles melting at 167° to 168° C. Overall yield: 42%.

Elemental analysis $C_{18}H_{16}ClN_3O$: Calculated C, 66.34; H, 4.95; N, 12.90. Found C, 66.04; H, 4.72; N, 12.54.

EXAMPLE 7

A mixture of 0.7 part of hydroxylamine hydrochloride, 4 volume parts water, 0.64 part of sodium carbonate, 10 volume parts of ethanol and 0.44 part of 5-chloro-2-(3-iodomethyl-5-methyl-s-triazol-4-yl) benzophenone is heated at 70° to 75° C for about one hour under stirring. Water is added to the mixture, and the whole mixture is extracted with chloroform. The chloroform layer is washed with water and dried over sodium sulfate, followed by distilling off the solvent. The residue is a mixture of 5-chloro-2-(3-hydroxyaminomethyl-5-methyl-s-triazol-4-yl) benzophenone and ring-closure product, 8-chloro-1-methyl-6-phenyl-4H-s-triazolo(4,3-a)(1,4) benzodiazepine 5N-oxide. Former compound is isolated as colorless crystals by treating the residue with ethyl acetate. Recrystallization from ethyl acetate gives colorless needles melting at 154° to 156° C. Isolation yield: 45%.

EXAMPLE 8

A solution of 0.33 part of 5-methyl-2-(3-chloromethyl-5-methyl-s-triazol-4-yl) benzophenone, 0.7 part of hydroxylamine hydrochloride, 0.6 part of sodium carbonate and 0.15 part of sodium iodide in 4 volume parts of water and 10 volume parts of ethanol is heated at 60° to 70° C for 3 hours under stirring. To the mixture are added 0.7 part of hydroxylamine hydrochloride and 0.5 part of sodium carbonate and the whole mixture is heated for further 2 hours. The resulting mixture is added to 20 volume parts of water and the whole mixture is extracted with chloroform. The chloroform layer is washed with water and dried over sodium sulfate, followed by distilling off the solvent. The residue is treated with ether, whereby crystals of 5-methyl-2-(3-hydroxylaminomethyl-5-methyl-s-triazol-4-yl) benzophenone are obtained. Recrystallization of the crystals from ethyl acetate gives colorless crystlas melting at 145° to 147° C. Yield: 81%.

Elemental analysis $C_{18}H_{18}N_4O_2$: Calculated: C, 67.06; H, 5.63; N, 17.38. Found: C, 66.88; H, 5.84; N, 16.95.

EXAMPLE 9

(a) A solution of 20 parts of 2-amino-2'-chlorobenzophenone, 15 parts of methyl orthoacetate, 12 volume parts of acetic acid in 250 parts of benzene is refluxed for 5 hours. The mixture is washed with saturated aqueous sodium bicarbonate solution and water, and then dried over sodium sulfate. Evaporation of the solvent gives 2'-chloro-2-(1-methoxyethylideneamino) benzophenone as an oily substance in almost quantitative yield.

To a solution of the oily product obtained above in 240 volume parts of ethanol are added 120 volume parts of hydrazine hydrate (100%) and 48 volume parts of acetic acid. After the solution is stirred for 20 hours at room temperature, 3-amino-4-(2-chlorophenyl)-3,4-dihydro-4-hydroxy-2-methylquinazoline separated from the solution as crystals is collected by filtration. Recrystallization from aqueous dimethylformamide gives colorless crystals melting at 211° to 213° C (decomposition). Yield 79%.

Elemental analysis $C_{15}H_{14}ClN_3O$: Calculated: C, 62.61, H, 4.90; N, 14.60. Found: C, 62.40, H, 4.99; N, 14.59.

(b) To a mixture of 29 parts of 3-amino-4-(2-chlorophenyl)-3,4-dihydro-4-hydroxy-2-methylquinazoline prepared above and 300 volume parts of dimethylformamide is added dropwise 23 volume parts of chloroacetylchloride. After stirring for 1 hour, the mixture is poured into an aqueous potassium carbonate solution (100 parts of potassium carbonate in 1500 volume parts of water) and then extracted with ethyl acetate. The ethyl acetate layer is washed with water and dried over sodium sulfate. After evaporation of the solvent, the residue is treated with benzene, whereby monocloroacetyl derivative of the starting compound is obtained as crystals. Recrystallization from ethyl acetate gives colorless prisms melting at 174.5° to 175.5° C (decomposition). Yield 69%.

Elemental analysis $C_{17}H_{13}Cl_2N_3O$: Calculated C, 58.97; H, 3.78; N, 12.14. Found C, 58.68; H, 3.73, N, 11.90.

(c) A solution of 19 parts of the monochloroacetyl derivative prepared above in 200 volume parts of 80% acetic acid is refluxed for 2.5 hours. After evaporation of the acetic acid, to the residue is added a saturated aqueous sodium bicarbonate solution and the mixture is extracted with chloroform. The chloroform layer is washed with water and dried over sodium sulfate. After evaporation of the solvent, the residue is treated with ethyl ether, whereby 2-(3-chloromethyl-5-methyl-s-triazol-4-yl)-2'-chlorobenzophenone is obtained as crystals. Recrystallization from ethanol gives colorless needles melting at 149.5° to 151° C. Yield 80%.

Elemental analysis $C_{17}H_{13}Cl_2N_3O$: Calculated: C, 58.97; H, 3.78; N, 12.14. Found: C, 58.86; H, 3.75; N, 11.97.

EXAMPLE 10

A mixture of 0.7 part of hydroxylamine hydrochloride, 4 volume parts of water, 0.6 part of sodium carbonate, 10 volume parts of ethanol and 0.44 part of 5-chloro-2-(3-iodomethyl-5-methyl-s-triazol-4-yl) benzophenone is heated at 70° to 80° C for about 1.5 hour under stirring. Water is added to the mixture, and the whole mixture is extracted with chloroform. The chloroform layer is washed with water and dried over sodium sulfate, followed by distilling off the solvent. The residue is dissolved in 10 volume parts of ethanol, and 0.2 volume parts of concentrated hydrochloric acid is added thereto. The whole mixture is heated at 70° C for 5 minutes, and the solvent is removed off under reduced pressure. The residue is neutralized with a saturated aqueous solution of sodium bicarbonate and then extracted with chloroform. The chloroform layer is washed with water and dried over sodium sulfate, followed by subjecting to distillation to remove the solvent. The residue is treated with ethyl acetate, whereby crystals of 8-chloro-1-methyl-6-phenyl-4H-s-triazolo(4,3-a)(1,4) benzodiazepine 5N-oxide are obtained. Recrystallization of the crystals from methanol gives colorless needles melting at 272° to 274° C (decomposition). Yield: 85%.

EXAMPLE 11

To a solution of 0.1 part of 5-chloro-2-(4-hydroxyaminomethyl-1-methyl-s-triazol-4-yl) benzophenone in 1 volume part of methanol is added one drop of concentrated hydrochloric acid, followed by keeping standing for 10 minutes at room temperature. The resultant is neutralized with a saturated aqueous solution of sodium bicarbonate, whereby crystals of 8-chloro-1-methyl-6-phenyl-4H-s-triazolo(4,3-a)(1,4) benzodiazepine 5N-oxide are obtained. Recrystallization of the crystals from methanol gives colorless needles melting at 271° to 272° C (decomposition). Yield: 98%.

The infrared absorption spectrum of the product is identical with that of the product obtained in example 10.

EXAMPLE 12

A mixture of 1.07 part of hydroxylamine hydrochloride, 4 volume parts water, 0.94 part of sodium carbonate, 10 volume parts of ethanol and 0.37 part of 5-chloro-2-(3-chloromethyl-s-triazol-4-yl) benzophenone hydrochloride is heated at 70° to 80° C for 4 hours. Water is added to the mixture, and the whole mixture is extracted with chloroform. The chloroform layer is washed with water and dried over sodium sulfate, followed by distilling off the solvent under reduced pressure. The residue is treated with ethyl acetate, whereby crystals of 8-chloro-6-phenyl-4-H-s-triazolo (4,3-a)(1,4) benzodiazepine 5N-oxide are obtained. Recrystallization from methanol-chloroform (1:1) gives colorless needles melting at 267° to 268° C (decomposition). Yield: 72%.

EXAMPLE 13

A solution of 1.2 part of 5-chloro-2-(3-chloromethyl-s-triazol-4-yl)-2'-chlorobenzophenone, 1.1 part of hydroxylamine hydrochloride and 1.1 part of sodium carbonate in 30 volume parts of ethanol is refluxed for 10 hours. Water is added to the mixture, and the whole mixture is extracted with chloroform. The chloroform layer is washed with water and dried over sodium sulfate, followed by distilling off the solvent. The residue is treated with ethyl acetate, whereby crystals of 8-chloro-6-(2-chlorophenyl)-4H-s-triazolo(4,3-a)(1,4) benzodiazepine 5N-oxide are obtained. Recrystallization from chloroform-methanol gives colorless needles melting at 273° to 274° C. Yield: 78.2%.

EXAMPLE 14

To a solution of 17.4 parts of hydroxylamine hydrochloride in 50 volume parts of water are added 3.75 parts of sodium iodide and 14.7 parts of sodium carbonate, and further to the mixture are added 8.1 parts of 5-methyl-2-(3-chloromethyl-5-methyl-s-triazol-4-yl) benzophenone and 200 volume parts of ethanol. The whole mixture is heated at 60° to 70° C for 4 hours under stirring, followed by subjecting to distillation to remove the solvent under reduced pressure. Water is added to the residue, and the mixture is extracted with chloroform. The chloroform layer is washed with water, followed by distilling off the solvent under reduced pressure. The residue is dissolved in 80 volume parts of ethanol, and 3 volume parts of concentrated hydrochloric acid is added thereto. The whole mixture is kept standing at room temperature for 1.5 hour, and then the solvent is distilled off. To the residue is added a saturated aqueous solution of sodium bicarbonate, whereby crystals of 1,8-dimethyl-6-phenyl-4H-s-triazolo (4,3-a)(1,4) benzodiazepine 5N-oxide are obtained. Recrystallization from methanol gives colorless needles melting at 256° to 257° C. Yield: 60.5%.

Elemental analysis $C_{18}H_{16}N_4O$: Calculated: C, 71.03; H, 5.30; N, 18.41. Found: C, 71.19; H, 5.27; N, 18.06.

EXAMPLE 15

A mixture of 116 parts of 2-amino-5-chlorobenzophenone, 116 parts of triethyl orthoacetate, 60 volume parts of acetic acid and 500 volume parts of benzene is heated under reflux for 40 minutes, and the solvent is evaporated under reduced pressure. To the solution of the above residue in 700 volume parts of ethanol are added 125 volume parts of hydrazine hydrate and 60 volume parts of acetic acid. After the mixture is allowed to stand at room temperature overnight, precipitated crystals of 3-amino-6-chloro-3,4-dihydro-4-hydroxy-2-methyl-4-phenylquinazoline are collected and washed with ethanol and ether (yield 132.7 parts).

To a mixture of the crystals obtained above and 303 parts of 2-methylimidazole and 2400 volume parts of dry benzene is added dropwise 150 volume parts of chloroacetyl chloride with stirring and cooling with ice-salt. The whole mixture is then stirred at room temperature for 2.5 hours and 750 volume parts of water is added thereto. The resulting crystals are collected by filtration, washed with water and benzene, dried (yield 144 parts) and dissolved in 2200 volume parts of formic acid. After the solution is refluxed for 2.5 hours, the formic acid is evaporated under reduced pressure, and to the residue is added saturated aqueous sodium bicarbonate solution. The mixture is extracted with ethyl acetate and the organic extract is washed with water and dried over sodium sulfate. Evaporation of the solvent leaves crystals which are then dissolved in 3400 volume parts of ethanol together with 240 parts of hydroxylamine hydrochloride, 200 parts of sodium carbonate, 50 parts of sodium iodide and 1350 volume parts of water. The resulting mixture is heated at 70° to 80° C for 3 hours with stirring. The mixture is concentrated, diluted with water and extracted with chloroform. The chloroform layer is washed with water and the solvent is evaporated. The residue is then dissolved in 1700 parts of ethanol, and 70 volume parts of concentrated hydrochloric acid is added thereto. The mixture is heated at 90° C for 10 minutes and concentrated, followed by neutralization with saturated aqueous sodium bicarbonate solution, whereby 8-chloro-1-methyl-5-phenyl-4H-s-triazolo (4,3-a)(1,4) benzodiazepine 5N-oxide are precipitated as crystals. The crystals are collected by filtration, washed with water, dried and recrystallized from methanol to give colorless needles melting at 270° to 274° C (decomposition). (yield 104 parts). Overall yield is 64% based on 2-amino-5-chlorobenzophenone.

EXAMPLE 16

A mixture of 69 parts of 2-(3-chloromethyl-5-methyl-s-triazol-4-yl)-2'-chlorobenzophenone, 69 parts of hydroxylamine hydrochloride, 66 parts of sodium carbonate and 1500 volume parts of ehtnanol is refluxed for 6.5 hours and kept standing for 3 days at room temperature. After filtration of the inorganic salt, the filtrate is acidified with concentrated hydrochloric acid and then heated for 30 minutes at 60° to 70° C. After evaporation of the solvent, to the residue is added a saturated aqueous sodium bicarbonate solution, and the mixture is extracted with chloroform. The chloroform layer is washed with water and dried over sodium sulfate. Evaporation of the solvent and treatment of the residue with ethyl acetate gives 6-(2-chlorophenyl)-1-methyl- 4H-s-triazolo [4,3-a][1,4] benzodiazepine 5N-oxide as crystals. Recrystallization from ethanol gives colorless prisms melting at 260° to 262° C (decomposition). Yield 72%.

Elemental analysis $C_{17}H_{13}ClN_4O_3$: Calculated: C, 62.87; H, 4.03; N, 17.25. Found: C, 62.40; H, 4.00; N, 17.02.

What we claim is:

1. A method for the production of a compound of the formula

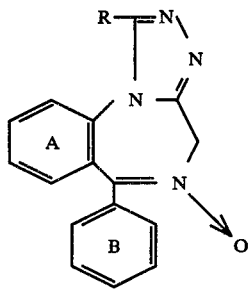

wherein R represents hydrogen or lower alkyl, and the rings A and/or B are unsubstituted or substituted by a member selected from the group consisting of halogen, nitro, trifluoromethyl, lower alkyl and lower alkoxy, which comprises reacting a compound of the formula

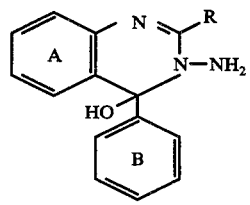

wherein R and the rings A and B have the same meanings as above, with a monohaloacetic acid halide or anhydride, to give a corresponding halogenoacetyl derivative, reacting the resulting halogenoacetyl derivative with a weak acid selected from the group consisting of formic acid, acetic acid, monochloroacetic acid, dichloroacetic acid, propionic acid, butyric acid, benzoic acid, salicyclic acid and phenylacetic acid, to give a compound of the formula

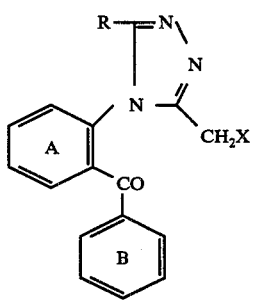

wherein R and the rings A and B have the same meanings as above, and X represents halogen, reacting the resulting compound with hydroxylamine to give a compound of the formula

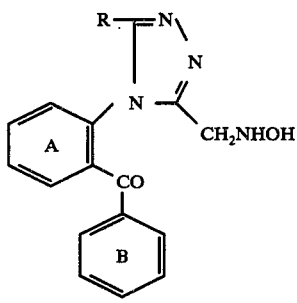

wherein R and the rings A and B have the same meanings as above, and subjecting a solution of the resulting compound to a temperature from about 10° C to the reflux temperature of the solution to effect ring closure.

2. A method for the production of a compound of the formula

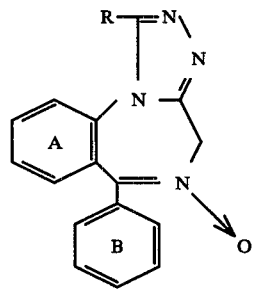

wherein R represents hydrogen or lower alkyl, and the rings A and/or B are unsubstituted or substituted by a member selected from the group consisting of halogen, nitro, trifluoromethyl, lower alkyl and lower alkoxy, which comprises reacting a compound of the formula

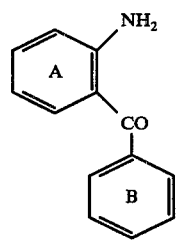

wherein the rings A and B have the same meanings as above, with an ortho ester of the formula $$RC(OR^2)_3$$

wherein each of R and $R^2$ represents hydrogen or lower alkyl, or an acylating agent selected from the group consisting of formic acid, acetic acid and the acid halides and anhydrides of an acid of the formula RCOOH wherein R represents hydrogen or lower alkyl, to give a compound of the formula

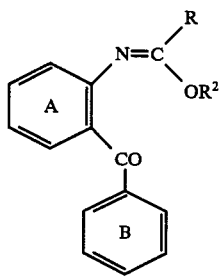

wherein R, R² and the rings A and B have the same meanings as above, reacting the resulting compound with hydrazine to give a compound of the formula

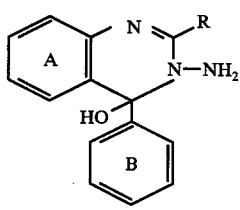

wherein R and the rings A and B have the same meanings as above, reacting the resulting compound with a monohaloacetic acid halide or anhydride, to give a corresponding halogenoacetyl derivative, reacting the resulting halogenoacetyl derivative with a weak acid selected from the group consisting of formic acid, acetic acid, monochloroacetic acid, dichloroacetic acid, propionic acid, butyric acid, benzoic acid, salicylic acid and phenylacetic acid, to give a compound of the formula

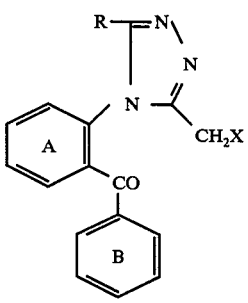

wherein R and the rings A and B have the same meanings as above, and X represents halogen, reacting the resulting compound with hydroxylamine to give a compound of the formula

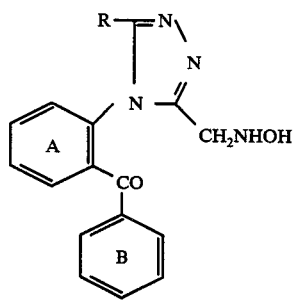

wherein R and the rings A and B have the same meanings as above, and subjecting a solution of the resulting compound to a temperature from about 10° C to the reflux temperature of the solution to effect ring closure.

3. A method for the production of a compound of the formula

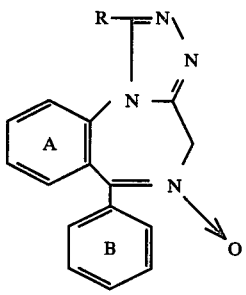

wherein R represents hydrogen or lower alkyl, and the rings A and/or B are unsubstituted or substituted by a member selected from the group consisting of halogen, nitro, trifluoromethyl, lower alkyl and lower alkoxy, which comprises reacting a compound of the formula

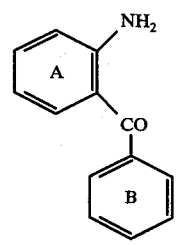

wherein the rings A and B have the same meanings as above, with a mixture of

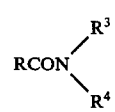

and POX₃, wherein R represents hydrogen or lower alkyl, X represents halogen and R³ and R⁴ are the same or different lower alkyl, to give a compound of the formula

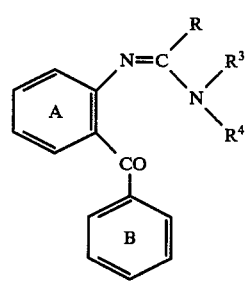

wherein the rings A and B have the same meanings as above, R represents hydrogen or lower alkyl, and R³ and R⁴ are the same or different lower alkyl, reacting the resulting compound with hydrazine to give a compound of the formula

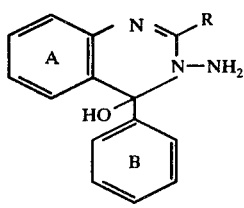

wherein R and the rings A and B have the same meanings as above, reacting the resulting compound with a monohaloacetic acid halide or anhydride, to give a corresponding halogenoacetyl derivative, reacting the resulting halogenoacetyl derivative with a weak acid selected from the group consisting of formic acid, acetic acid, monochloroacetic acid, dichloroacetic acid, propionic acid, butyric acid, benzoic acid, salicylic acid and phenylacetic acid, to give a compound of the formula

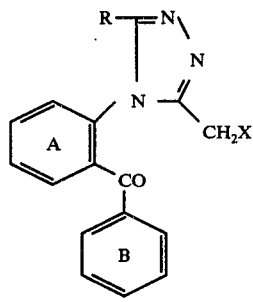

wherein R and the rings A and B have the same meanings as above, and X represents halogen, reacting the resulting compound with hydroxylamine to give a compound of the formula

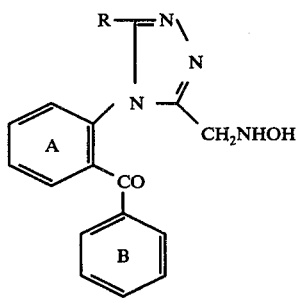

wherein R and the rings A and B have the same meanings as above, and subjecting a solution of the resulting compound to a temperature from about 10° C to the reflux temperature of the solution to effect ring closure.

* * * * *